United States Patent
Kim et al.

(10) Patent No.: US 12,404,532 B2
(45) Date of Patent: *Sep. 2, 2025

(54) COMPOSITION FOR PRODUCING GLUCOSYLATED STEVIOL GLYCOSIDE INCLUDING GLUCOSYLTRANSFERASE AND METHOD OF PRODUCING GLUCOSYLATED STEVIOL GLYCOSIDE USING THE SAME

(71) Applicant: CJ CHEILJEDANG CORPORATION, Seoul (KR)

(72) Inventors: Jungeun Kim, Seoul (KR); Sunghee Park, Seoul (KR); Tae Joo Yang, Seoul (KR); Sun Chu, Seoul (KR); Seong Bo Kim, Seoul (KR); Eun Jung Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 669 days.

This patent is subject to a terminal disclaimer.

(21) Appl. No.: 17/610,352

(22) PCT Filed: Jun. 8, 2020

(86) PCT No.: PCT/KR2020/007396
§ 371 (c)(1),
(2) Date: Nov. 10, 2021

(87) PCT Pub. No.: WO2020/251228
PCT Pub. Date: Dec. 17, 2020

(65) Prior Publication Data
US 2022/0220523 A1    Jul. 14, 2022

(30) Foreign Application Priority Data
Jun. 14, 2019 (KR) .................. 10-2019-0070925

(51) Int. Cl.
*C12P 19/18* (2006.01)
*C12P 19/56* (2006.01)

(52) U.S. Cl.
CPC ............... *C12P 19/18* (2013.01); *C12P 19/56* (2013.01)

(58) Field of Classification Search
CPC .................. C12P 19/18; C12P 19/56
See application file for complete search history.

(56) References Cited

U.S. PATENT DOCUMENTS

2020/0383364 A1    12/2020   Yang et al.

FOREIGN PATENT DOCUMENTS

EP    3 708 672 A1    9/2020
JP    2009-034080 A    2/2009
(Continued)

OTHER PUBLICATIONS

Devlamynck et al., "Trans-α-glucosylation of stevioside by the mutant glucansucrase enzyme Gtf180-ΔN-Q1140E improves its taste profile," *Food Chemistry* 272:653-662 (2019).

(Continued)

*Primary Examiner* — Louise W Humphrey
*Assistant Examiner* — Rachel Emily Martin
(74) *Attorney, Agent, or Firm* — Seed Intellectual Proper Law Group LLP (57) ABSTRACT

The present disclosure relates to a composition for producing glucosylated steviol glycoside, the composition including glucosyltransferase including an amino acid sequence of SEQ ID NO: 1; and a method of producing glucosylated steviol glycoside using the same.

8 Claims, 5 Drawing Sheets

Specification includes a Sequence Listing.

(56) References Cited

FOREIGN PATENT DOCUMENTS

| JP | 2018-139613 A | 9/2018 |
|---|---|---|
| KR | 1995-0002868 B1 | 3/1995 |
| KR | 10-1199821 B1 | 11/2012 |
| KR | 10-2013-0014227 A | 2/2013 |
| KR | 10-2018-0055735 A | 5/2018 |
| UY | 38008 A | 1/2019 |
| WO | 2016/144175 A1 | 9/2016 |
| WO | 2018/093196 A1 | 5/2018 |

OTHER PUBLICATIONS

Gerwig et al., "Structural analysis of rebaudioside A derivatives obtained by *Lactobacillus reuteri* 180 glucansucrase-catalyzed trans-α-glucosylation," *Carbohydrate Research 440-441*:51-62 (2017).

Te Poele et al., "Glucansucrase (mutant) enzymes from *Lactobacillus reuteri* 180 efficiently transglucosylate *Stevia* component rebaudioside A, resulting in a superior taste," *Nature—Scientific Reports 8*:1516, 12 pages (2018).

Uniprot, UniProtKB/TrEMBL, Accession No. A0A0RZFDFZ_9LAC0, 1 page, Jan. 20, 2016.

SEQUENCE LISTING

<160> NUMBER OF SEQ ID NOS: 1

<210> SEQ ID NO 1
<211> LENGTH: 734
<212> TYPE: PRT
<213> ORGANISM: Lactobacillus mali

<400> SEQUENCE: 1

```
Met Asp Gln Met Val Leu Glu Thr Gln Gln Trp Leu Asn Lys Thr Tyr
1               5                   10                  15

Gly Gly Val Ser Gly Phe Gly Ser Val Thr Glu Asp Gly Leu Thr Gly
            20                  25                  30

Trp Gly Thr Val Tyr Gly Leu Thr Arg Ala Leu Gln His Glu Leu Gly
        35                  40                  45

Ile Thr Gly Leu Val Asn Asn Phe Gly Pro Thr Ser Lys Gln Lys Phe
    50                  55                  60

Asn Asn Ile Ala Lys Thr Ile Val Val Gly Tyr Thr Gly Asn Ile Ala
65                  70                  75                  80

Tyr Ile Ile Gln Gly Gly Phe Trp Cys Lys Gly Ile Thr Pro Gly Glu
                85                  90                  95

Phe Asp Gly Lys Phe Ser Ala Asp Thr Ala Ser Ala Val Thr Thr Met
            100                 105                 110

Lys Thr Lys Ala Gly Leu Ala Asp Thr Ser Ser Val Asp Gly Asn
            115                 120                 125

Phe Met Ala Ala Leu Leu Asn Met Ser Ser Phe Asp Leu Leu Thr Gly
        130                 135                 140

Gly Asp Ser Lys Val Arg Glu Met Gln Gln Gln Leu Asn His Asp Tyr
145                 150                 155                 160

Leu Ala Tyr Thr Gly Ile Leu Pro Cys Asp Gly Ile Tyr Gln Arg Asp
                165                 170                 175

Thr Asn Ser Ala Leu Ile Tyr Ala Leu Gln Ala Glu Glu Lys Ile Ser
            180                 185                 190

Thr Ser Val Ala Thr Gly Ala Tyr Gly Ala Thr Thr Lys Lys Asp Thr
        195                 200                 205

Pro Thr Val Lys Glu Gly Thr Thr Asn Asn Phe Val Arg Ile Leu Gln
    210                 215                 220

Trp Gly Leu Tyr Val Asn Asn Lys Ala Tyr Thr Gly Ala Phe Asp Gly
225                 230                 235                 240

Val Tyr Asp Ser Ala Val Val Ala Ala Val Lys Glu Phe Glu Glu Thr
                245                 250                 255

Met Ala Leu Asp Ser Thr Asp Gly Thr Ser Ala Gly Val Asp Ile Phe
            260                 265                 270

Met Ser Leu Leu Thr Ser Ala Gly Asn Pro Asp Arg Ser Ala Ile Ala
        275                 280                 285

Cys Asp Thr Ser Tyr Gln Leu Asn Ala Thr Arg Val Ala Thr Leu Lys
    290                 295                 300

Asn Ala Gly Tyr Ser Ile Val Gly Arg Tyr Leu Thr Gly Thr Val Gly
305                 310                 315                 320

Ser Gly Thr Ser Glu Arg Ala Lys Asn Leu Thr Thr Asp Glu Ile Thr
                325                 330                 335

Ala Ile Thr Thr Gly Gly Leu Lys Ile Phe Pro Ile Tyr Gln Asp Gly
            340                 345                 350

Ala Ser Asp Lys Glu Ala Tyr Phe Thr Ala Ala Gln Gly Lys Thr Asp
        355                 360                 365
```

-continued

```
Gly Thr Lys Ala Val Tyr Ala Ala Gln Asp Leu Gly Phe Lys Glu Gly
    370             375                 380

Val Val Ile Tyr Phe Ala Val Asp Ala Asp Ile Gln Ala Gly Asp Ile
385             390                 395                 400

Ala Gly Ser Ala Lys Val Tyr Phe Glu Ala Leu Tyr Asp Ile Val Thr
            405                 410                 415

Ser Tyr Gly Tyr Glu Val Gly Ile Tyr Gly Thr Arg Asn Val Ser Ala
            420                 425                 430

Thr Ile Ile Ser Ala Gly Leu Ala Thr Lys Ala Phe Ile Ser Asp Met
        435                 440                 445

Ser Thr Gly Tyr Ser Gly Asn Leu Gly Tyr Ser Ile Pro Asp Glu Trp
    450                 455                 460

Ala Phe Asp Gln Phe Ser Glu Ile Ser Ile Gly Asp Phe Ala Ile Asp
465                 470                 475                 480

Lys Asp Ala Thr Thr Ser Ala Arg Glu Thr Ala Thr Gly Ser Phe Gly
                485                 490                 495

Val Gly Gly Glu Ser Gly Tyr Gly Asn Ala Glu Asp Leu Ala Lys Ile
            500                 505                 510

Asn Thr Ile Ile Asp Ala Leu Ser Gln Lys Lys Asn Phe Ser Tyr Leu
        515                 520                 525

Ser Gly Leu Lys Ile Glu Lys Thr Ser Lys Glu Tyr Glu Ile Pro Gly
    530                 535                 540

Phe Ala Val Asp Phe Tyr Val Gln Val Lys Phe Glu Ala Ser Val Ser
545                 550                 555                 560

Glu Pro Gly Asp Asn Val Gly Val Val Tyr Asn Val Ser Asn Gly Lys
                565                 570                 575

Phe Glu Ser Asp Phe Thr Asp Thr Ile Ala Gly Val Val Ala Leu Ser
                580                 585                 590

Asp Glu Ile Asn Lys Glu Asp Ile Asn Ser Ala Leu Thr Glu Leu Ser
            595                 600                 605

Ser Leu Ile Asn Asn Gly Gln Ile Trp Val Glu Pro Val Thr Lys Gly
    610                 615                 620

Ser Asp Ala Gly Ile Ala Leu His Ile Lys Ser Thr Phe Asp His Thr
625                 630                 635                 640

Leu Asp Ser Gly Glu Thr Ile Glu Leu Glu Tyr Glu Ile Ile Ile Asp
                645                 650                 655

Glu Ile Phe His Lys Ile Glu Val Val Pro Thr Gly Val Pro Asn Thr
                660                 665                 670

Thr Ala Asn Asp Tyr Asn Ser Leu Phe Pro Asn Gly Ile Lys Glu Phe
            675                 680                 685

Val Gly Phe Ser Ile Val Ala Gly Leu Ala Thr Gly Gly Ile Tyr Tyr
    690                 695                 700

Val Val Thr Ala Val Gly Ala Thr Ala Ala Val Val Thr Thr Ser Ile
705                 710                 715                 720

Leu Ala Leu Ile Ala Leu Leu Lys Asn Asn Asp Thr Gly Val
                725                 730
```

COMPOSITION FOR PRODUCING GLUCOSYLATED STEVIOL GLYCOSIDE INCLUDING GLUCOSYLTRANSFERASE AND METHOD OF PRODUCING GLUCOSYLATED STEVIOL GLYCOSIDE USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_481USPC_SEQUENCE_LISTING.txt. The text file is 6.2 KB, was created on Nov. 9, 2021, and is being submitted electronically via EFS-Web.

TECHNICAL FIELD

The present disclosure relates to a composition for producing glucosylated steviol glycoside, the composition including glucosyltransferase; and a method of producing glucosylated steviol glycoside using the same.

BACKGROUND ART

As the World Health Organization (WHO) recommends lowering the amount of daily sugar intake due to concerns about disease (obesity) caused by sugar consumption, various policies aimed at reducing the amount of sugar intake are actively being discussed by the governments of developed countries. Therefore, as the need for developing various alternative sweeteners is increasing in the market, alternative sweeteners are continuously being developed and commercialized. As alternative sweeteners, these are the subject of continuous variation in the form of synthetic high-intensity sweeteners (e.g., Saccharin, Aspartame, Sucralose, etc.), synthetic sugar alcohols (e.g., Maltitol and Xylitol), and high-intensity sweeteners (e.g., Rebaudioside A and Liquorice). Nevertheless, due to concerns over the safety of synthetic sweeteners, customers' need for natural sweeteners has been steadily increasing; however, because of limitations to peculiar flavor properties of natural sweeteners (i.e., off-smell and off-flavor), natural sweeteners cannot fully replace existing low-calorie and zero-calorie products based on synthetic sweeteners.

A natural high-intensity sweetener that has received considerable attention in recent years is *stevia* extracted from the leaves of *Stevia rebaudiana* Bertoni. *Stevia* is a natural material, the sweetness of which is 200 to 300 times that of sugar, and consists of Stevioside, Rebaudioside A, Rebaudioside B, Rebaudioside C, Rebaudioside D, Rebaudioside E, Rebaudioside M, etc. In addition, *stevia* has no calories and positive effects on blood glucose and insulin levels, and has been reported to have no adverse effects in the human body. However, although *stevia* has potential to be used as an alternative sweetener, it has limitations in application due to the disadvantage that it expresses strong bitter taste.

Methods for improving sweetness of *stevia* include a method of transferring a saccharide using an enzyme. As the method, a method of transferring 1 to 12 glucose molecules to a steviol glycoside using CGTase is widely used in the art (Korean Patent Application No. 10-1991-0020769). However, the method has a disadvantage in that the glucose structure transferred to the steviol glycoside is $\alpha$-(1,4) and is all degraded by intestinal microorganisms, thereby increasing calories.

DISCLOSURE

Technical Problem

Under such circumstances, the present inventors have completed the present disclosure by confirming that an enzyme derived from *Lactobacillus mali* transfers glucose to steviol glycoside via an $\alpha$-(1,6) bond to produce indigestible glucosylated steviol glycoside.

Technical Solution

An object of the present disclosure is to provide a composition for producing glucosylated steviol glycoside, the composition including glucosyltransferase including an amino acid sequence of SEQ ID NO: 1, a microorganism expressing the glucosyltransferase, or a culture of the microorganism.

Another object of the present disclosure is to provide a method of producing glucosylated steviol glycoside, the method including the step of contacting steviol glycoside with the glucosyltransferase including the amino acid sequence of SEQ ID NO: 1, the microorganism expressing the glucosyltransferase, or the culture of the microorganism.

Still another object of the present disclosure is to provide glucosylated steviol glycoside produced by the above production method.

Still another object of the present disclosure is to provide a sweetener composition including the glucosylated steviol glycoside.

Still another object of the present disclosure is to provide a composition for improving sweetness, the composition including the glucosyltransferase including the amino acid sequence of SEQ ID NO: 1, the microorganism expressing the glucosyltransferase, or the culture of the microorganism.

Still another object of the present disclosure is to provide a method of improving sweetness of steviol glycoside, the method including the step of converting steviol glycoside into glucosylated steviol glycoside using the glucosyltransferase including the amino acid sequence of SEQ ID NO: 1, the microorganism expressing the glucosyltransferase, or the culture of the microorganism.

Advantageous Effects

The composition of the present disclosure for producing glucosylated steviol glycoside and the method of the present disclosure for producing glucosylated steviol glycoside employ glucosyltransferase including an amino acid sequence of SEQ ID NO: 1, thereby specifically producing glucosylated steviol glycoside.

Additionally, since the glucosyltransferase has a high conversion rate of glucosylated steviol glycoside from steviol glycoside, it is possible to very efficiently produce glucosylated steviol glycoside.

BEST MODE FOR CARRYING OUT THE INVENTION

Hereinbelow, the present disclosure will be described in detail. Meanwhile, each of the explanations and exemplary embodiments disclosed herein may be applied to other explanations and exemplary embodiments. That is, all combinations of various factors disclosed herein belong to the scope of the present disclosure. Furthermore, the scope of the present disclosure should not be limited by the specific disclosure provided hereinbelow.

In order to achieve the objects, an aspect of the present disclosure provides a composition for producing glucosylated steviol glycoside, the composition including glucosyltransferase including an amino acid sequence of SEQ ID NO: 1, a microorganism expressing the glucosyltransferase, or a culture of the microorganism.

As used herein, the "glucosyltransferase" refers to an enzyme that transfers glucose from a glucose donor to a glucose acceptor.

The glucosyltransferase may have a use for producing glucosylated steviol glycoside by transferring glucose from a glucose donor to steviol glycoside.

The glucosyltransferase may be an enzyme including the amino acid sequence of SEQ ID NO: 1. The enzyme including the amino acid sequence of SEQ ID NO: 1 may be used interchangeably with an enzyme having the amino acid sequence of SEQ ID NO: 1, an enzyme essentially consisting of the amino acid sequence of SEQ ID NO: 1, or an enzyme consisting of the amino acid sequence of SEQ ID NO: 1.

Further, although the glucosyltransferase in the present disclosure is defined as the enzyme including the amino acid sequence of SEQ ID NO: 1, it does not exclude a mutation that may occur by adding a meaningless sequence upstream or downstream the amino acid sequence of SEQ ID NO: 1, a naturally occurring mutation, or a silent mutation, and it is apparent to those skilled in the art that as long as a protein has activity identical to or corresponding to that of the enzyme including the amino acid sequence of SEQ ID NO: 1, essentially consisting of the amino acid sequence of SEQ ID NO: 1, or consisting of the amino acid sequence of SEQ ID NO: 1, it corresponds to the glucosyltransferase of the present disclosure. For specific example, the glucosyltransferase of the present disclosure may be a protein consisting of the amino acid sequence of SEQ ID NO: 1, or a protein consisting of an amino acid sequence having 80%, 90%, 95%, or 97% or more homology or identity thereto. Additionally, it is obvious that any protein having an amino acid sequence with deletion, modification, substitution, or addition in part of the sequence may also be included in the scope of the glucosyltransferase of the present disclosure, as long as the amino acid sequence has a homology or identity described above and exhibits efficacy corresponding to that of the enzyme.

That is, although described as "an enzyme or protein having an amino acid sequence of a particular SEQ ID NO" or "an enzyme or protein consisting of an amino acid sequence of a particular SEQ ID NO" in the present disclosure, it is obvious that any protein having an amino acid sequence with deletion, modification, substitution, or addition in part of the sequence may also be used in the present disclosure, as long as the protein may have an activity identical or corresponding to that of a polypeptide including the amino acid sequence of the corresponding SEQ ID NO. For example, it is obvious that any "polypeptide consisting of the amino acid sequence of SEQ ID NO: 1" may belong to "the polypeptide including the amino acid sequence of SEQ ID NO: 1", as long as it has an activity identical or corresponding to that of the polypeptide including the amino acid sequence of SEQ ID NO: 1.

As used herein, the term "homology" or "identity" refers to a degree of matching with two given amino acid sequences or nucleotide sequences, and may be expressed as a percentage. The terms "homology" and "identity" may often be used interchangeably with each other.

The homology or identity of conserved polynucleotide or polypeptide sequences may be determined by standard alignment algorithms and may be used with a default gap penalty established by the program being used. Substantively, homologous or identical sequences may generally hybridize under moderate or high stringent conditions, along the entire length or at least about 50%, about 60%, about 70%, about 80%, or about 90% of the entire length of the sequences. Polynucleotides that contain degenerate codons instead of codons in the hybridizing polynucleotides are also considered.

Whether any two polynucleotide or polypeptide sequences have a homology, similarity, or identity may be determined using a known computer algorithm such as the "FASTA" program (e.g., Pearson et al., (1988)[Proc. Natl. Acad. Sci. USA 85]: 2444) using default parameters. Alternately, it may be determined using the Needleman-Wunsch algorithm (Needleman and Wunsch, 1970, J. Mol. Biol. 48: 443-453), which is performed in the Needleman program of the EMBOSS package ((EMBOSS: The European Molecular Biology Open Software Suite, Rice et al., 2000, Trends Genet. 16: 276-277) (version 5.0.0 or later) (GCG program package (Devereux, J., et al., Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego, 1994, and [CARILLO ETA/.](1988) SIAM J Applied Math 48: 1073). For example, the homology, similarity, or identity may be determined using BLAST or ClustalW of the National Center for Biotechnology Information.

The homology, similarity, or identity of polynucleotide or polypeptide sequences may be determined by comparing sequence information using, for example, the GAP computer program (e.g., Needleman et al., (1970), J Mol Biol. 48: 443), as published in Smith and Waterman, Adv. Appl. Math (1981) 2:482. In summary, the GAP program defines the homology, similarity, or identity as the value obtained by dividing the number of similarly aligned symbols (i.e., nucleotides or amino acids) by the total number of the symbols in the shorter of the two sequences. Default parameters for the GAP program may include (1) a unary comparison matrix (containing a value of 1 for identities and 0 for non-identities) and the weighted comparison matrix of Gribskov et al (1986) Nucl. Acids Res. 14: 6745, as disclosed in Schwartz and Dayhoff, eds., Atlas Of Protein Sequence And Structure, National Biomedical Research Foundation, pp. 353-358 (1979) (or EDNAFULL (EMBOSS version of NCBI NUC4.4) substitution matrix); (2) a penalty of 3.0 for each gap and an additional 0.10 penalty for each symbol in each gap (or a gap opening penalty of 10 and a gap extension penalty of 0.5); and (3) no penalty for end gaps.

Further, whether any two polynucleotide or polypeptide sequences have a homology, similarity, or identity may be determined by comparing sequences by Southern hybridization experiments under defined stringent conditions, and the defined appropriate hybridization conditions may be within a range in the art and may be determined by a method well known to those skilled in the art (e.g., J. Sambrook et al., Molecular Cloning, A Laboratory Manual, 2nd Edition, Cold Spring Harbor Laboratory press, Cold Spring Harbor, New York, 1989; F. M. Ausubel et al., Current Protocols in Molecular Biology, John Wiley & Sons, Inc., New York).

The glucosyltransferase including the amino acid sequence of SEQ ID NO: 1 may be an enzyme derived from the genus *Lactobacillus*, and specifically, an enzyme derived from *Lactobacillus mali*, but is not limited thereto.

The glucosyltransferase including the amino acid sequence of SEQ ID NO: 1 may have a conversion rate of 50% or more, specifically 60% or more, more specifically 70% or more, much more specifically 80% or more, and even much more specifically 90% or more from steviol glycoside into glucosylated steviol glycoside, but is not limited thereto.

The composition of the present disclosure for producing glucosylated steviol glycoside may include a microorganism expressing the glucosyltransferase including the amino acid sequence of SEQ ID NO: 1, or a culture of the microorganism.

The microorganism may be specifically a microorganism of the genus *Lactobacillus*, and more specifically *Lactobacillus mali*, but is not limited thereto, as long as it is a microorganism that may include or express the glucosyltransferase of the present disclosure.

Specifically, the culture may be a culture including the microorganism expressing the glucosyltransferase including the amino acid sequence of SEQ ID NO: 1, or a culture from which the microorganism is excluded.

The composition of the present disclosure for producing glucosylated steviol glycoside may further include steviol glycoside and a glucose donor.

The "steviol glycoside", which is one of natural sweeteners, may be represented by Chemical Formula 1 below.

[Chemical Formula 1]

In Chemical Formula 1, to $R_1$, hydrogen (H) may be bound, or 1 to 3 glucose molecules may be bound via a β-bond; and to $R_2$, one molecule of glucose, xylose, or rhamnose may be bound via a β-bond, and 0 to 2 glucose molecules may be bound thereto via a β-bond, but they are not limited thereto.

The steviol glycoside may be one or more selected from the group consisting of Stevioside, Rubusoside, Dulcoside A, Rebaudioside A, Rebaudioside C, Rebaudioside D, Rebaudioside E, Rebaudioside F, and Rebaudioside M, but is not limited thereto.

The glucose donor may be any one of an oligomer of glucose, a polymer of glucose, or a cyclic form thereof which may be reacted in the presence of glucosyltransferase such that one or more glucose molecules may be transferred to the steviol glycoside, and specifically, it may be sugar, but is not limited thereto.

The "glucosylated steviol glycoside" may be in the form in which glucose is linked to steviol glycoside.

Specifically, the glucosylated steviol glycoside may be in the form in which glucose is linked to steviol glycoside via an α-(1,6) bond.

Specifically, the glucosylated steviol glycoside may be in the form in which glucose is linked via an α-(1,6) bond to glucose linked at 19-OH position of steviol glycoside.

Specifically, the glucosylated steviol glycoside may be in the form in which 1 to 3 glucose molecules are linked to steviol glycoside.

The composition of the present disclosure for producing glucosylated steviol glycoside may further include a cofactor capable of advantageously transferring glucose to steviol glycosides or capable of enhancing stability of the composition, but is not limited thereto. Examples of the cofactor may include metal ions, metal salts, excipients, preservatives, etc., but are not limited thereto.

To achieve the above object, another aspect of the present disclosure provides a method of producing glucosylated steviol glycoside, the method including the step of contacting steviol glycoside with the glucosyltransferase including the amino acid sequence of SEQ ID NO: 1, the microorganism expressing the glucosyltransferase, or the culture of the microorganism.

The "glucosyltransferase including the amino acid sequence of SEQ ID NO: 1", "microorganism", "culture", and "glucosylated steviol glycoside" are the same as described above.

The method of the present disclosure for producing glucosylated steviol glycoside may include the step of reacting a glucose donor (e.g., sugar) and steviol glycoside in the presence of the glucosyltransferase including the amino acid sequence of SEQ ID NO: 1, the microorganism expressing the glucosyltransferase, or the culture of the microorganism. In this regard, the "glucose donor" and "steviol glycoside" are the same as described above.

The step of reacting the glucose donor and steviol glycoside may be carried out at pH of 1 to 10, specifically at pH of 2 to 9, more specifically at pH of 3 to 8, and much more specifically at pH of 5 to 6, but is not limited thereto.

The step of reacting the glucose donor and steviol glycoside may be carried out at 1° C. to 80° C., specifically at 5° C. to 70° C., more specifically at 25° C. to 50° C., and much more specifically at 35° C. to 45° C., but is not limited thereto.

Further, the step of reacting the glucose donor and steviol glycoside may be carried out at pH of 1 to 10, pH of 2 to 9, pH of 3 to 8, or pH of 5 to 6, and at 1° C. to 80° C., 5° C. to 70° C., 25° C. to 50° C., or 35° C. to 45° C., but is not limited thereto.

The method of the present disclosure for producing glucosylated steviol glycoside may further include the step of recovering glucosylated steviol glycoside. The recovery may employ various methods known in the art, for example, filtration, size-exclusion chromatography, ion-exchange chromatography, crystallization, HPLC, etc., but is not limited thereto. Further, the recovery step may include a purification process.

To achieve the above object, still another aspect of the present disclosure provides glucosylated steviol glycoside produced by the method of the present disclosure for producing glucosylated steviol glycoside.

The "glucosylated steviol glycoside" is the same as described above.

Specifically, the glucosylated steviol glycoside may be one or more selected from the group consisting of glucosylated Stevioside, glucosylated Rubusoside, glucosylated Dulcoside A, glucosylated Rebaudioside A, glucosylated Rebaudioside C, glucosylated Rebaudioside D, glucosylated Rebaudioside E, glucosylated Rebaudioside F, and glucosylated Rebaudioside M, but is not limited thereto.

To achieve the above object, still another aspect of the present disclosure provides a sweetener composition including the glucosylated steviol glycoside of the present disclosure.

The sweetener composition of the present disclosure may have an improved bitter taste and improved solubility, as compared with a sweetener composition including steviol glycoside.

The improved bitter taste may be a reduced bitter taste. The improved solubility may be increased solubility.

To achieve the above object, still another aspect of the present disclosure provides a composition for improving sweetness of steviol glycoside, the composition including the glucosyltransferase including the amino acid sequence of SEQ ID NO: 1, the microorganism expressing the glucosyltransferase, or the culture of the microorganism.

The "glucosyltransferase including the amino acid sequence of SEQ ID NO: 1", "microorganism", "culture", and "steviol glycoside" are the same as described above.

The sweetness improvement may be bitter taste improvement due to reduced bitter taste.

To achieve the above object, still another aspect of the present disclosure provides a method of improving sweetness of steviol glycoside, the method including the step of converting steviol glycoside into glucosylated steviol glycoside using the glucosyltransferase including the amino acid sequence of SEQ ID NO: 1, the microorganism expressing the glucosyltransferase, or the culture of the microorganism.

The "glucosyltransferase including the amino acid sequence of SEQ ID NO: 1", "microorganism", "culture", "steviol glycoside", and "glucosylated steviol glycoside" are the same as described above.

The converting step may be carried out at pH of 1 to 10, specifically at pH of 2 to 9, more specifically at pH of 3 to 8, and much more specifically at pH of 5 to 6, but is not limited thereto.

The converting step may be carried out at 1° C. to 80° C., specifically at 5° C. to 70° C., more specifically at 25° C. to 50° C., and much more specifically at 35° C. to 45° C., but is not limited thereto.

Further, the converting step may be carried out at pH of 1 to 10, pH of 2 to 9, pH of 3 to 8, or pH of 5 to 6, and at 1° C. to 80° C., 5° C. to 70° C., 25° C. to 50° C., or 35° C. to 45° C., but is not limited thereto.

The sweetness improvement may be bitter taste improvement due to reduced bitter taste.

DETAILED DESCRIPTION OF THE INVENTION

Hereinafter, the present disclosure will be described in more detail with reference to Examples and Experimental Examples. However, these Examples and Experimental Examples are only for illustrating the present disclosure, and the scope of the present disclosure is not intended to be limited by these Examples and Experimental Examples.

Example 1: Purification of Enzyme

A test tube was filled with 5 mL of MRS broth (BD Difco), and then *Lactobacillus mali* was seeded thereto, followed by incubation at 30° C. and 180 rpm for 15 hours.

Thereafter, a 250 mL flask was filled with 100 mL of MRS broth, and then the culture broth was seeded thereto at a concentration of 5% (v/v), followed by incubation at 30° C. and 180 rpm for 15 hours.

Thereafter, a 3 L fermentor was filled with 1 L of modified MRS broth, and then the culture broth was seeded thereto at a concentration of 5% (v/v), followed by incubation at 30° C. and 300 rpm for 24 hours. At this time, a composition of the modified MRS broth is the same as in Table 1 below.

TABLE 1

| Composition | Unit (g/L) | Content | Manufacturer |
| --- | --- | --- | --- |
| Sucrose | g | 20 | SIGMA |
| Polypeptone | g | 10 | DAEJUNG |
| Yeast extract | g | 5 | BD Difco |
| Beef extract | g | 10 | BD Difco |
| Ammonium citrate | g | 2 | DAEJUNG |
| Sodium acetate | g | 5 | DAEJUNG |
| $K_2HPO_4$ | g | 2 | DAEJUNG |
| $MgSO_4$—$7H_2O$ | g | 0.1 | JUNSEI |
| $MnSO_4$—$H_2O$ | g | 0.05 | JUNSEI |
| Tween 80 | g | 1 | DAEJUNG |

The culture broth was centrifuged at 13,000 rpm for 15 minutes to recover a supernatant. The supernatant was subjected to dialysis using a 20 mM Tris-HCl, pH 7.4 buffer to perform protein purification.

In primary purification, anion-exchange chromatography was used, and Hitrap™ DEAE FF (GE healthcare) column was used. The sample was loaded onto the column at a flow rate of 1 mL/min, followed by elution using a 20 mM Tris-HCl, pH 7.4 buffer containing 1 M NaCl.

In secondary purification, gel filtration chromatography was used, and Hiload™ 16/60 Superdex 200 pg (GE healthcare) column was used. Purification was carried out using a 20 mM Tris-HCl buffer containing 150 mM NaCl.

Figure 1:
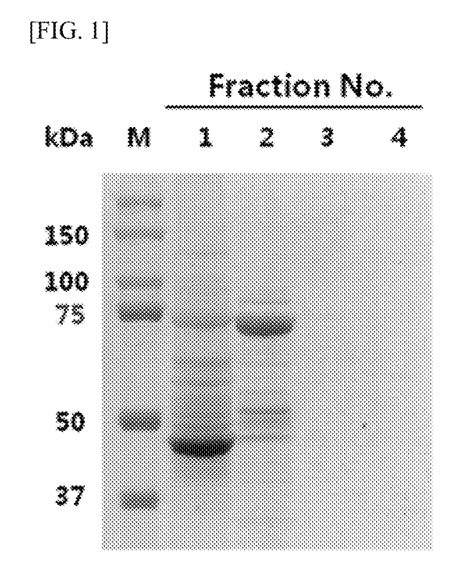
FIG. 1 shows SDS-PAGE results of proteins in four kinds of fractions purified from a culture of *Lactobacillus mali*.

From the above purification, four kinds of fractions were obtained, and SDS-PAGE results of the respective fractions are shown in FIG. 1.

Example 2: Examination of Activity of Enzyme

To confirm the presence of the desired enzyme, sugar hydrolysis activity of each fraction was examined by a reducing sugar determination method (DNS method).

A 200 mM sugar solution and each fraction were mixed at a ratio of 1:1 in a 50 mM sodium acetate buffer, and allowed to react in a water bath at 40° C. for 10 minutes, followed by inactivation at 100° C. A DNS reagent was added thereto at a ratio of 1:3, and then mixed and allowed to react at 100° C. for 5 minutes, and then DNS reaction was immediately stopped on ice. Thereafter, optical density (OD) of the DNS reagent was measured at 575 nm, and the activity was confirmed from a constructed fructose standard curve. At this time, 1 unit is defined by the amount (mL) of an enzyme that produces 1 μmole of fructose per 1 minute.

As a result, it was confirmed that a 75 kDa protein of Fraction No. 2 had sugar hydrolysis activity.

Example 3: Identification of Enzyme

The 75 kDa protein was identified by LC-MS.

Example 3-1: Pretreatment of Sample (in Gel Trypsin Digestion)

For protein identification using mass spectrometry (MS), fragmentation of the protein to be analyzed into peptides is needed.

Therefore, the gel corresponding to 75 kDa of fraction #2 of FIG. 1 was cut, and then a 50% CH$_3$CN(H$_2$O) solvent was added to the in-gel piece sample, and destained by reacting for 15 minutes. Thereafter, 2 μL of 1 M dithiothreitol (DTT, GE) dissolved in a 50 mM ammonium bicarbonate (ABC, SIGMA) buffer was added, and stored at room temperature for 1 hour. Then, 4 μL of 1 M iodoacetamide (IAA, SIGMA) dissolved in a 50 mM ammonium bicarbonate (ABC, SIGMA) buffer was added, and stored in the dark at room temperature for 1 hour. 1 μg of a trypsin solution (Sequencing-grade modified porcine trypsin, Thermofisher, Madison, WI, USA) was added to the destained in-gel piece sample, and allowed to react at 37° C. for 16 hours. 200 μL of a 50% CH$_3$CN(H$_2$O) solvent was added to recover the hydrolyzed peptides through gel dehydration, which were then dried using a SpeedDry vacuum concentrator. In order to remove salts and other impurities, desalting was carried out using C18 Ziptip (Millipore).

Example 3-2: Liquid Chromatography-Mass Spectrometry (LC-MS)

Liquid chromatography-mass spectrometry was performed using Ultimate 3000 RS UHPLC, Q-Exactive Orbitrap (Thermo Scientific) mass spectrometer, and analysis conditions are as follows:
(1) Chromatography: Thermo (Dionex) UHPLC Ultimate 3000
(2) Column: Acclaim prepMap™ RSLC 50 μm×15 cm, nanoviper C18, 2 μm, 100 A
(3) Solvent: A=distilled water (containing 0.1% formic acid), B=acetonitrile (containing 0.1% formic acid)
(4) Elution conditions

TABLE 2

| Time (min) | A (%) | B (%) |
|---|---|---|
| 0 | 95 | 5 |
| 5 | 95 | 5 |
| 63 | 70 | 30 |
| 68 | 50 | 50 |
| 70 | 20 | 80 |
| 73 | 20 | 80 |
| 75 | 95 | 5 |
| 88 | 95 | 5 |
| 89 | 95 | 5 |

(5) Flow rate: 0.2 μL/min
(6) Sample injection: 1 μL

Thereafter, amino acid sequences were examined by de novo peptide sequencing, and at this time, Proteome Discoverer 2.1 (Thermo) was used as an analysis program.

The thus-confirmed amino acid sequence was SEQ ID NO: 1.

Example 4: Examination of Activity of Crude Enzyme Solution of Transferring Glucose to Steviol Glycoside 6% Rebaudioside A (purecircle) or 6% Stevioside (carbosynth), and 6% white sugar (CJ CheilJedang) were dissolved in a 50 mM sodium acetate buffer (pH 5.0), and then the *Lactobacillus mali* crude enzyme solution including the enzyme including the amino acid sequence of SEQ ID NO: 1 was added thereto, and allowed to react at 40° C. for 24 hours. Thereafter, whether glucosylated Rebaudioside A or glucosylated Stevioside was produced was confirmed by HPLC, and the results are shown in FIGS. 2 to 5. Meanwhile, HPLC analysis conditions are as follows:

TABLE 3

| | |
|---|---|
| Mobile phase | Acetonitrile (30%):Distilled water (70%) |
| Column | 250 × 4.6 mm Capcell pak C18 MG II (Shiseido) |
| Flow rate | 0.6 mL/min |
| Temperature | 30° C. |
| Injection amount | 20 μL |
| Detector | DAD (210 nm) |

Figure 2:
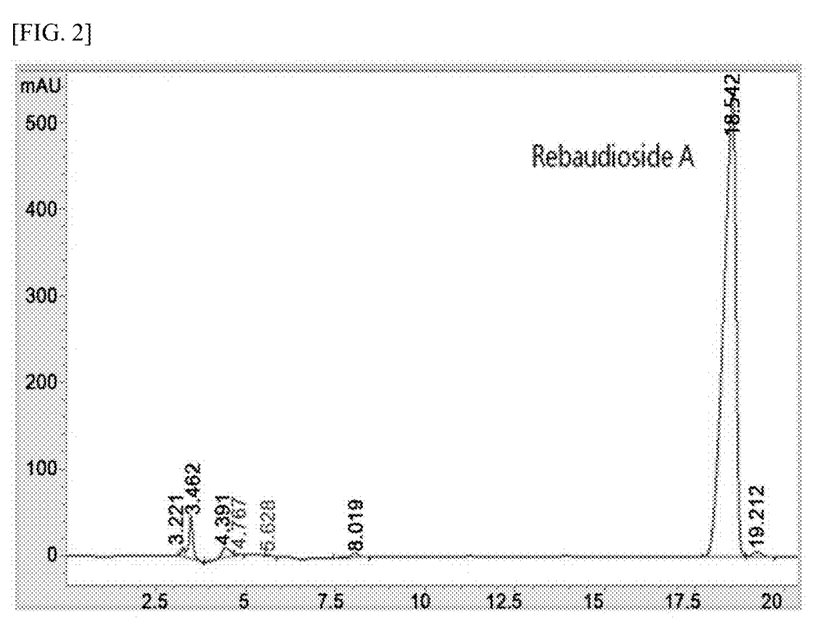
FIG. 2 shows HPLC results before reacting Rebaudioside A and sugar with a crude enzyme solution of *Lactobacillus mali*.
Figure 3:
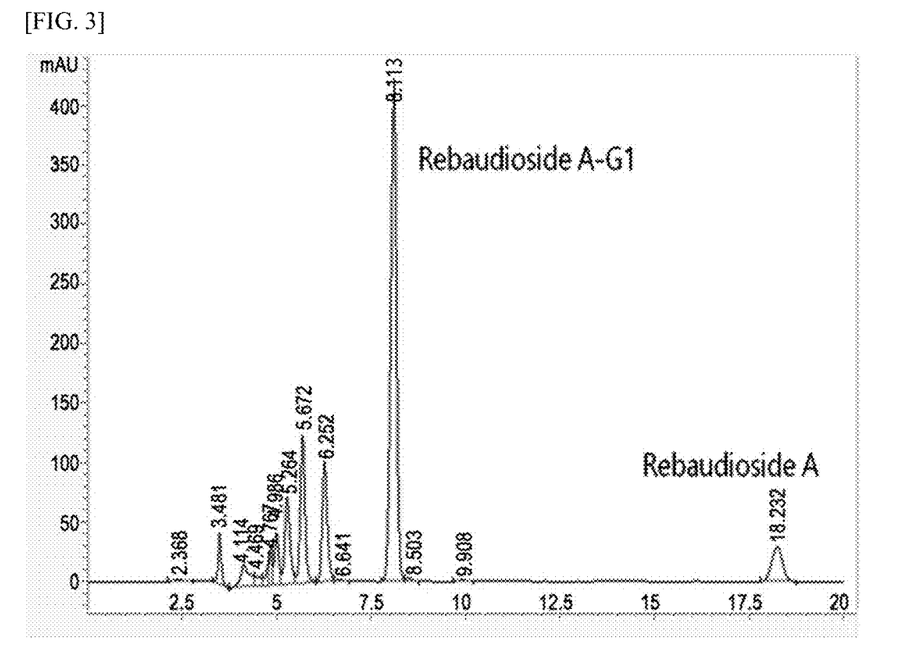
FIG. 3 shows HPLC results after reacting Rebaudioside A and sugar with the crude enzyme solution of *Lactobacillus mali*.
Figure 4:
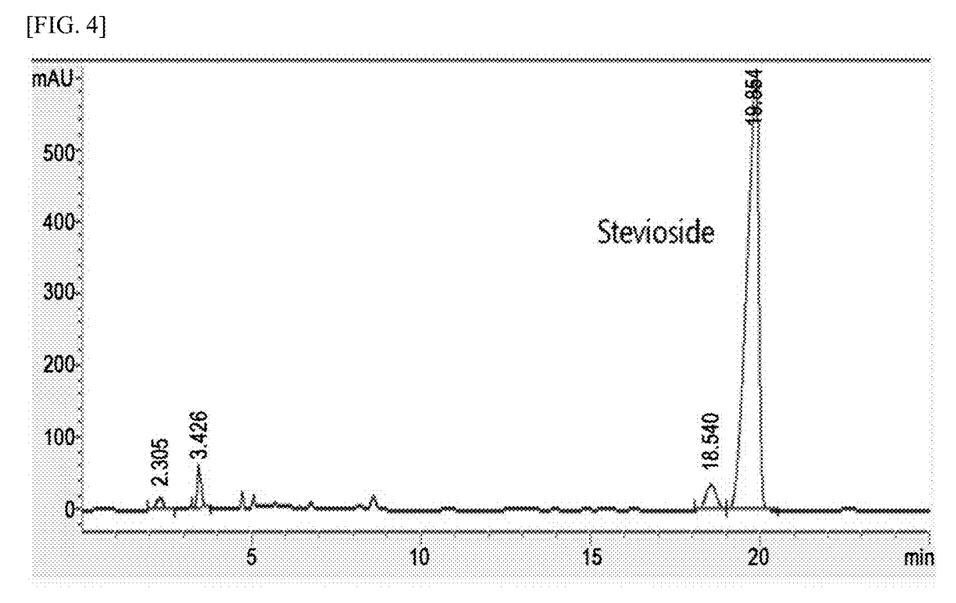
FIG. 4 shows HPLC results before reacting Stevioside and sugar with the crude enzyme solution of *Lactobacillus mali*.
Figure 5:
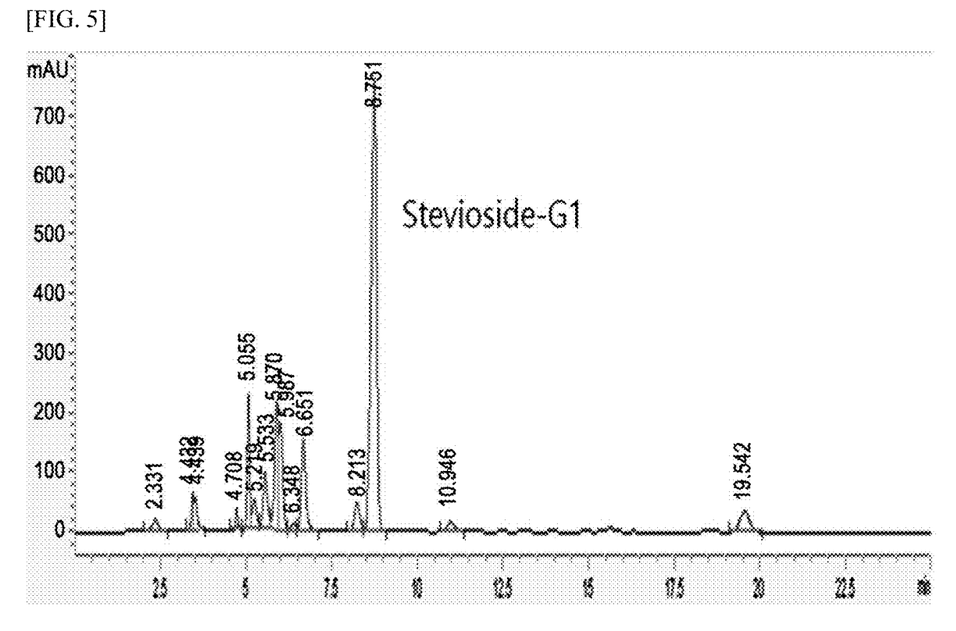
FIG. 5 shows HPLC results after reacting Stevioside and sugar with the crude enzyme solution of *Lactobacillus mali*.

FIGS. 2 and 4 show HPLC analysis results before the enzyme reaction, and FIGS. 3 and 5 show HPLC analysis results after the enzyme reaction.

Comparison of FIGS. 2 and 3 showed that Rebaudioside A was converted into glucosylated Rebaudioside A (Rebaudioside A-G1) by the enzyme reaction. At this time, it was confirmed that the conversion rate was about 90%.

Further, comparison of FIGS. 4 and 5 showed that Stevioside was converted into glucosylated Stevioside (Stevidoside-G1) by the enzyme reaction. At this time, it was confirmed that the conversion rate was about 90%.

Meanwhile, it was confirmed by NMR that the glucosylated Stevioside (Stevidoside-G1) and the glucosylated Rebaudioside A (Rebaudioside A-G1) were produced by transferring one glucose molecule via an α-(1,6) bond to glucose linked at 19-OH position of Stevioside and Rebaudioside A, respectively.

Example 5: Examination of Activity of Enzyme Including Amino Acid Sequence of SEQ ID NO: 1 of Transferring Glucose to Steviol Glycoside The activity of the enzyme including the amino acid sequence of SEQ ID NO: 1, which was confirmed in Example 3, was examined. Specifically, it was examined whether the enzyme has activity of transferring glucose to steviol glycoside.

Example 5-1: Preparation of Microorganism Including Enzyme and Purification of Enzyme A polynucleotide encoding the amino acid sequence of SEQ ID NO: 1 was prepared by a polynucleotide synthesis method (Bioneer Corp.), and the obtained polynucleotide was inserted into a pBT7-N-His vector, which was then transformed into *E. coli* BL21(DE3). The transformed *E.*

*coli* was smeared on a plate medium containing ampicillin to obtain a recombinant strain (microorganism).

Meanwhile, the microorganism was deposited at the Korean Culture Center of Microorganisms, which is an international depositary authority under the Budapest Treaty, on Jun. 11, 2019, as Accession No. KCCM12561P.

The recombinant *E. coli* strain was seeded in 5 mL of an LB medium containing ampicillin, and seed culture was carried out at 37° C. until optical density at 600 nm reached 2.0. The seed culture broth was added to 500 mL of an LB medium containing ampicillin, and main culture was carried out. Thereafter, when optical density at 600 nm reached 0.4, 0.1 mM isopropyl β-D-thiogalactopyranoside (IPTG) was added to induce mass-expression of the enzyme including the amino acid sequence of SEQ ID NO: 1. During the process, an agitation speed was 180 rpm, and culture temperature was maintained at 37° C. After IPTG addition, the agitation speed was 120 rpm, and culture temperature was maintained at 16° C.

The culture broth was centrifuged at 10,000×g at 4° C. for 20 minutes to obtain a cell pellet. A 50 mM tris-HCl buffer solution was added to the pellet, and re-suspended as a cell solution. The cell solution was sonicated using a sonicator. The cell lysate was centrifuged at 13,000×g at 4° C. for 20 minutes to collect a supernatant only. Thereafter, the enzyme was purified using a Ni-NTA superflow column.

Example 5-2: Examination of Enzyme Activity

6% Rebaudioside A (purecircle) and 6% white sugar (CJ CheilJedang) were dissolved in a 50 mM sodium acetate buffer (pH 5.0), and then the enzyme including the amino acid sequence of SEQ ID NO: 1, which was obtained in Example 5-1, was added thereto, and allowed to react at 40° C. for 24 hours. Thereafter, whether glucosylated Rebaudioside A was produced was confirmed by HPLC, and the results are shown in FIGS. 6 and 7.

Figure 6:
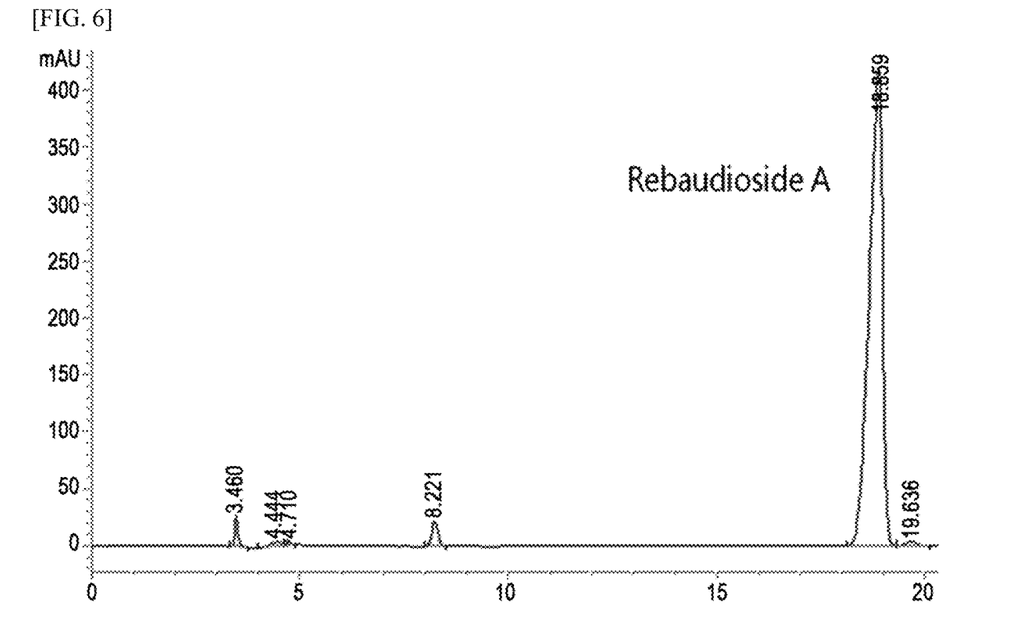
FIG. 6 shows HPLC results before reacting Rebaudioside A and sugar with an enzyme including an amino acid sequence of SEQ ID NO: 1.
Figure 7:
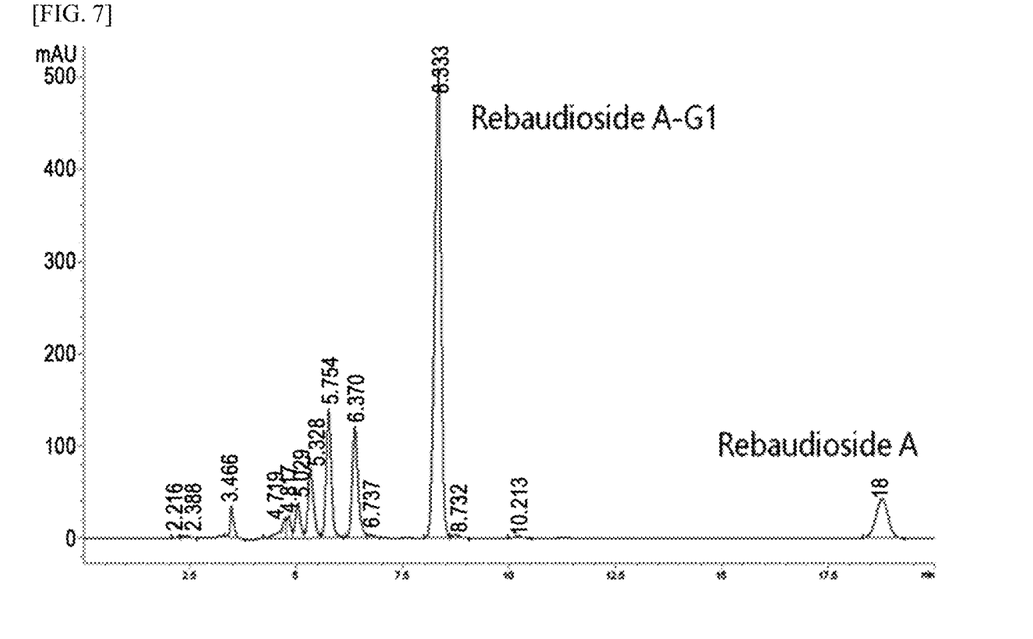
FIG. 7 shows HPLC results after reacting Rebaudioside A and sugar with the enzyme including the amino acid sequence of SEQ ID NO: 1.

FIG. 6 shows HPLC analysis results before the enzyme reaction, and FIG. 7 shows HPLC analysis results after the enzyme reaction.

Comparison of FIGS. 6 and 7 showed that Rebaudioside A was converted into glucosylated Rebaudioside A (Rebaudioside A-G1) by the enzyme reaction. At this time, it was confirmed that the conversion rate was about 90%.

Meanwhile, it was confirmed by NMR that the glucosylated Rebaudioside A (Rebaudioside A-G1) was produced by transferring one glucose molecule via an α-(1,6) bond to glucose linked at 19-OH position of Rebaudioside A.

That is, it was confirmed that the enzyme including the amino acid sequence of SEQ ID NO: 1 had activity identical to that of the crude enzyme solution of *Lactobacillus mali* of Example 4.

Example 6: Evaluation of Solubility of Glucosylated Steviol Glycoside

The solubility of steviol glycoside and glucosylated steviol glycoside was measured.

Specifically, the solubility of Rebaudioside A (RA), Stevioside (STV), glucosylated Rebaudioside A (RA-Glu) of Example 4, and glucosylated Stevioside (STV-Glu) of Example 4 was measured, respectively.

Each 6 g of Rebaudioside A, Stevioside, glucosylated Rebaudioside A, and glucosylated Stevioside was mixed with 10 mL, and then dissolved by sonication at 50° C. for 60 minutes. The resultant was incubated for 1 week in a water bath at 5° C., 15° C., 25° C., 35° C., 45° C., or 55° C.

Thereafter, the resulting solution was centrifuged at 12,000 rpm for 10 minutes, and 1 mL of the supernatant was collected and dried in an oven at 105° C. to measure the solubility, which is shown in Table 4.

TABLE 4

| Temperature | Solubility (%) | | | |
|---|---|---|---|---|
| (° C.) | STV | RA | STV-Glu | RA-Glu |
| 5 | 6.3 | 1.1 | 40 ↑ | 40 ↑ |
| 15 | 6.2 | 0.6 | 40 ↑ | 40 ↑ |
| 25 | 5.3 | 0.3 | 40 ↑ | 40 ↑ |
| 35 | 9.2 | 0.5 | 40 ↑ | 40 ↑ |
| 45 | 13.7 | 1.1 | 40 ↑ | 40 ↑ |
| 55 | 39.7 | 1.6 | 40 ↑ | 40 ↑ |

According to the results of Table 4, it can be seen that the glucosylated Stevioside and the glucosylated Rebaudioside A showed remarkably increased solubility, as compared with Stevioside and Rebaudioside A, respectively.

Example 7: Evaluation of Sweetness and Quality of Sweetness of α-(1,6) Glucosylated Rebaudioside A The known material (i.e., α-(1,4) glucosylated Rebaudioside A) and the α-(1,6) glucosylated Rebaudioside A of Example 4 were independently dissolved in water and provided to panels for evaluation of actual sweetness and quality of sweetness. The results are shown in Table 5 below.

TABLE 5

| Sample | Actual Sweetness | Evaluation of Quality of Sweetness |
|---|---|---|
| α-(1,4) glucosylated Rebaudioside A | 19 | Bitter taste is stronger than sweet taste, has greasy taste like starch syrup. Weak off-smell compared to α-(1,6) glucosylated Rebaudioside A, but strong off-flavor. |
| α-(1,6) glucosylated Rebaudioside A | 26 | Gives sweet taste in the beginning, has a bit of bitter taste, but has clean taste. Has off-smell (alcohol smell, etc.). |

As shown in Table 5, it was confirmed that the α-(1,6) glucosylated Rebaudioside A showed high sweetness, as compared with the α-(1,4) glucosylated Rebaudioside A, and also had better quality of sweetness.

Based on the above description, it will be understood by those skilled in the art that the present disclosure may be implemented in a different specific form without changing the technical spirit or essential characteristics thereof. Therefore, it should be understood that the above embodiment is not limitative, but illustrative in all aspects. The scope of the disclosure is defined by the appended claims rather than by the description preceding them, and therefore all changes and modifications that fall within metes and bounds of the claims, or equivalents of such metes and bounds are therefore intended to be embraced by the claims.

What is claimed is:

1. A method of producing a glucosylated steviol glycoside, the method comprising the step of contacting a steviol glycoside with a glucosyltransferase including an amino acid sequence of SEQ ID NO:1, a microorganism expressing the glucosyltransferase, or a culture of the microorganism.

2. The method of claim 1, the method comprising the step of reacting a glucose donor and steviol glycoside in the presence of the glucosyltransferase including the amino acid sequence of SEQ ID NO: 1, the microorganism expressing the glucosyltransferase, or the culture of the microorganism.

3. The method of claim 2, wherein the reacting is carried out at pH of 1 to 10.

4. The method of claim 2, wherein the reacting is carried out at 1° C. to 80° C.

5. The method of claim 1, wherein the glucosylated steviol glycoside is in the form in which glucose is linked to steviol glycoside via an α-(1,6) bond.

6. The method of claim 5, wherein the glucosylated steviol glycoside is in the form in which glucose is linked via an α-(1,6) bond to glucose linked at 19-OH position of steviol glycoside.

7. The method of claim 1, wherein the glucosylated steviol glycoside is in the form in which 1 to 3 glucose molecules are linked to steviol glycoside.

8. The method of claim 1, wherein the steviol glycoside is one or more selected from the group consisting of Stevioside, Rubusoside, Dulcoside A, Rebaudioside A, Rebaudioside C, Rebaudioside D, Rebaudioside E, Rebaudioside F, and Rebaudioside M.

* * * * *